(12) United States Patent
Mirzazadeh et al.

(10) Patent No.: US 10,398,847 B2
(45) Date of Patent: Sep. 3, 2019

(54) INCREMENTAL SYRINGE

(71) Applicant: Wake Forest University Health Sciences, Winston-Salem, NC (US)

(72) Inventors: Majid Mirzazadeh, Winston-Salem, NC (US); Philip J. Brown, Winston-Salem, NC (US); Kenneth W. Russell, Winston-Salem, NC (US)

(73) Assignee: Wake Forrest University Health Sciences, Winston-Salem, NC (US)

( * ) Notice: Subject to any disclaimer, the term of this patent is extended or adjusted under 35 U.S.C. 154(b) by 339 days.

(21) Appl. No.: 14/966,326

(22) Filed: Dec. 11, 2015

(65) Prior Publication Data

US 2016/0166772 A1 Jun. 16, 2016

Related U.S. Application Data

(60) Provisional application No. 62/091,248, filed on Dec. 12, 2014.

(51) Int. Cl.
*A61M 5/315* (2006.01)

(52) U.S. Cl.
CPC ...... *A61M 5/3157* (2013.01); *A61M 5/31513* (2013.01); *A61M 5/31526* (2013.01);
(Continued)

(58) Field of Classification Search
CPC ............ A61M 5/3157; A61M 5/31513; A61M 5/31526; A61M 5/31573; A61M 5/31595;
(Continued)

(56) References Cited

U.S. PATENT DOCUMENTS 288,828 A 11/1883 McElroy
4,654,035 A * 3/1987 Ando ................ A61M 5/31555
604/210

(Continued)

FOREIGN PATENT DOCUMENTS

DE 102015000999 7/2016
EP 0959916 B1 11/2003

(Continued)

OTHER PUBLICATIONS

Imed M et al. Hybrid linear incremental actuator for biomedical systems. Int. J. Emerg. Sci. Mar. 2012; 2(1): 103-122.

(Continued)

*Primary Examiner* — Laura A Bouchelle
*Assistant Examiner* — Dung T Ulsh
(74) *Attorney, Agent, or Firm* — Stoel Rives LLP (57) ABSTRACT

An incremental syringe useful for multiple injections of medications like botulinum toxin is provided. The syringe includes detents on the syringe plunger which provide a tactile feeling, a discrete audible sound or "click," or preferably both, for every unit of medication aspirated or injected to or from an individual syringe. Hence, there is no need to look at the syringe, or bring it to the eye level, during use thereof. In some embodiments, a second set of detents is included, and in some embodiments a third set of detents is included. Syringe plungers useful for combining with a syringe body to produce such an incremental syringe are also described.

25 Claims, 9 Drawing Sheets

(52) U.S. Cl.
CPC .... *A61M 5/31573* (2013.01); *A61M 5/31595* (2013.01); *A61M 2005/31508* (2013.01); *A61M 2205/581* (2013.01); *A61M 2205/582* (2013.01)

(58) Field of Classification Search
CPC .. A61M 2005/31508; A61M 2205/581; A61M 2205/582; A61M 5/31511; A61M 5/502; A61M 5/315; A61M 5/31501
See application file for complete search history.

(56) References Cited

U.S. PATENT DOCUMENTS

| | | | |
|---|---|---|---|
| 7,351,224 B1 | 4/2008 | Shaw | |
| 7,611,495 B1 | 11/2009 | Gianturco | |
| 9,186,464 B2 * | 11/2015 | Franklin | A61M 5/31526 |
| 2006/0161106 A1 | 7/2006 | Wu | |
| 2006/0184136 A1 * | 8/2006 | Kleyman | A61M 5/31595 604/210 |
| 2009/0287161 A1 * | 11/2009 | Traub | A61M 5/31595 604/208 |
| 2010/0240003 A1 * | 9/2010 | Fritze | A46B 9/005 433/80 |
| 2011/0009829 A1 | 1/2011 | Kosinski et al. | |
| 2012/0253291 A1 * | 10/2012 | Ivosevic | A61M 5/31513 604/222 |
| 2012/0316509 A1 * | 12/2012 | Kayser | A61M 5/19 604/210 |
| 2013/0090603 A1 * | 4/2013 | Hoyle, Jr. | A61M 5/3129 604/189 |
| 2013/0197449 A1 * | 8/2013 | Franklin | A61M 5/31526 604/209 |
| 2013/0274367 A1 * | 10/2013 | Minagawa | C08F 2/38 522/129 |
| 2014/0193773 A1 * | 7/2014 | Rolle | A61C 19/063 433/83 |
| 2014/0288507 A1 * | 9/2014 | Samuel | A61M 5/31513 604/222 |
| 2015/0057638 A1 | 2/2015 | Davidian et al. | |
| 2015/0359969 A1 * | 12/2015 | Armstrong | A61M 5/31505 604/221 |
| 2016/0166774 A1 * | 6/2016 | Leary | A61M 5/3135 604/506 |
| 2016/0331904 A1 * | 11/2016 | Huthmacher | A61M 5/3157 |
| 2017/0000942 A1 * | 1/2017 | Gonnelli | A61M 5/31526 |
| 2017/0354779 A1 * | 12/2017 | Atterbury | A61M 5/2033 |

FOREIGN PATENT DOCUMENTS

| | | |
|---|---|---|
| GB | 958636 | 5/1964 |
| GB | 1225495 | 3/1991 |
| WO | 2010132290 | 11/2010 |
| WO | 2013132192 | 9/2013 |

OTHER PUBLICATIONS

Lteif AN and Schwenk WF. Accuracy of pen injectors versus insulin syringes in children with type 1 diabetes. Diabetes Care. Jan. 1999; 22(1): 137-140.

Shenot PJ and Mark Jr. Intradetrusor onabotulinumtoxinA injection: how I do it. The Canadian Journal of Urology. Feb. 2013; 20(1): 6649-6655.

Product Reference Guide 2010. Insulin Pens. Diabetes Health. www.DiabetesHealth.com, 2 pp.

Stryker® Instruments product reference guide. Revolution cement mixing system. www.stryker.com, 6 pp.

Becton, Dickinson and Company. Syringe and needle history. (2004) 8 pp.

Olsen JL et al. Prentice Hall Companion Website online study guide. Medical Dosage Calculations, Chapter 7, Syringes. www.prenhall. com/olsen, retrieved Dec. 11, 2015.

International Search Report and Written Opinion, PCT/US2015/065298, dated Mar. 11, 2016.

European Search Report dated Jul. 9, 2018 for EP158668517.

* cited by examiner

FIG. 15
(PREFERRED
AMOUNG 10-15)

INCREMENTAL SYRINGE

RELATED APPLICATIONS

This application claims the benefit of U.S. provisional patent application Ser. No. 62/091,248, filed Dec. 12, 2014, the disclosure of which is incorporated by reference herein in its entirety.

FIELD OF THE INVENTION

The present invention concerns medical syringes for injection of active agents such as botulinum toxin and local anesthetics into a subject, at multiple sites but through the same syringe and injection needle assembly.

BACKGROUND OF THE INVENTION

The commonplace, seemingly straightforward, task of administering an injection of medication with a syringe is often more complicated than it first appears. With syringes in common use by clinicians today, when a certain amount of medication is to be taken from a bottle (vial), the clinician inserts the syringe needle into the bottle, brings the bottle up to eye level, aspirates or withdraws slightly more than the required amount of medication from the bottle into the syringe, and then gradually injects a portion of the medication from the syringe back into the bottle until the desired amount of medication is contained in the syringe. Often, as the user tries to gradually empty the syringe contents back into the bottle, more medication than intended is inadvertently returned to the bottle. As a result, the clinician must either inject less medication than desired, or repeat the process again. If the clinician cannot bring the bottle to eye level (as when aspirating from a large or hanging container), the process is much more difficult and inaccurate, because of different angle of vision.

When the clinician wishes to inject only a portion of the medication contained in the syringe, the process is even more complicated. To be more accurate the clinician should bend forward and look at the plunger level to make sure how much has been injected. If more than intended has been injected, there is no way to bring it back—a particularly dangerous situation when injecting more critical medications.

There are some occasions where an expensive medication like botulinum toxin, or a critical and potentially dangerous medication like lidocaine, should be injected with multiple, repeated, injections. With conventional syringes, there is no way one person can do so accurately. Many times, injection should be done while looking at monitor; so it is not possible to look at the syringe at the same time. Furthermore it is extremely difficult to inject a specific amount to one point. (See, e.g., P. Shenot and J. Mark, Intradetrusor onabotulinumtoxinA injection: how I do it, The Canadian Journal of Urology, 20(1), 6649 (February 2013)). This means that, most of the time, there should be another person to help with starting and stopping injections at specific volumes. Still it is common that, in any spots more than needed amount of Botox is injected and at the end there is nothing left for other areas. This practice is neither effective nor efficient. Accordingly, there is a need for new syringe designs that aid the clinician in more efficiently and effectively carrying out these procedures.

SUMMARY OF THE INVENTION

In view of the foregoing, we designed and describe a new syringe—an incremental syringe—to replace syringes in common usage and especially for multiple injections of expensive medications like botulinum toxin.

With this newly designed syringe there is preferably a tactile feeling, a discrete audible sound or "click," or preferably both, for every unit of medication aspirated or injected to or from an individual syringe. Hence, there is no need to look at the syringe, or bring it to the eye level (or to bend forward to be able to see the scale on it). Also injecting certain amount of medication in different spots is much easier, accurate and efficient.

Accordingly, a first aspect of the invention is a syringe, comprising:

(a) an elongate hollow body having a first open end, an inside wall, a second open end, and a raised lip on the inside wall;

(b) a syringe plunger positioned in the hollow body through the second open end, the plunger comprising:
   (i) an elongate shaft having a longitudinal axis, an upper end portion and a lower end portion;
   (ii) a seal connected to the lower end portion (e.g., with the seal configured to engage the body inside wall and eject a liquid contained in the hollow body through the first opening when the plunger is depressed into the hollow body);
   (iii) a flange connected to the upper end portion; and
   (iv) a first set of detents (e.g., raised detents—including fixed raised detents and/or flexible leaf detents—as well as recessed detents) formed on the elongate shaft in a linear and uniformly spaced pattern thereon aligned with the longitudinal axis, with each member of the first set of detents symmetric with one another and configured to sequentially and releasably engage the lip when the plunger is depressed into the hollow body;

the syringe having a total injectable volume, with the first set of detents preferably configured to divide the total injectable volume into a plurality of separate, preferably uniform, injectable subvolumes.

In some embodiments, each of the first set of detents comprises a flexible leaf (e.g., a generally flat or leaf-shaped member formed on and projecting laterally from the elongate shaft, which may be tapered, and/or connected to the elongate shaft by means of a "living hinge" region).

In some embodiments, the elongate shaft comprises at least three (e.g., four) elongate ribs joined along the longitudinal axis.

In some embodiments, the first set of detents is formed on at least two of the elongate ribs (e.g., as in the disk-shaped embodiment, where the first set are formed on all of the elongate ribs).

In some embodiments, the first set of detents is formed on only one of the elongate ribs.

In some embodiments, each of the first set of detents comprises:

a raised detent having a leading edge portion and a trailing edge portion, both of which are aligned with the longitudinal axis, with the slope of the trailing edge portion being greater than the slope of the leading edge portion;

a recessed detent having a leading edge portion and a trailing edge portion, both of which are aligned with the longitudinal axis, with the slope of the trailing edge portion being less than the slope of the leading edge portion.

Some embodiments of the foregoing further comprise a second set of detents (e.g., raised detents—including fixed raised detents and/or flexible leaf detents—as well as recessed detents) formed on the elongate shaft in a linear and uniformly spaced pattern thereon aligned with the longitudinal axis, with the second set of detents positioned in offset alignment with the first set of detents, the first and second set of detents together configured to define on the elongate shaft: (i) a plurality of uniformly sized, injection segments (e.g., segments in which the plunger substantially freely slides in the hollow body so as to permit the operator to inject an incremental portion of the syringe contents contained within that one incremental region, each segment delivering one of the injectable subvolumes), and (ii) a plurality of uniformly sized trapping segments in sequential alternating arrangement with the incremental injection segments (e.g., with a trapping segment being a segment in which resistance to further plunger movement is encountered by the operator at the conclusion of the previous injection segment, and which requires further or additional pressure on the plunger to enter the next incremental injection segment and initiate discharge of the contents of the syringe defined by the next or following incremental injection portion).

In some embodiments, the elongate shaft comprises at least three (e.g., three or four) elongate ribs joined along the longitudinal axis; the first set of detents are formed on only one of the elongate ribs, or the second set of detents are formed on at least two of the elongate ribs (e.g., as in the disk-shaped embodiment, where the first set are formed on all of the elongate ribs (and the first set of detents and the second set of detents are formed on the same, or different, elongate ribs.

In some embodiments of the foregoing, each of the second set of detents comprises: a raised detent having a leading edge portion and a trailing edge portion, both of which are aligned with the longitudinal axis, with the slope of trailing edge portion being less than the slope of the leading edge portion; or a recessed detent having a leading edge portion and a trailing edge portion, both of which are aligned with the longitudinal axis, with the slope of trailing edge portion being greater than the slope of the leading edge portion.

In some embodiments of the foregoing, the first set of detents and the second set of detents are (optionally aligned with and) substantially symmetric with one another in reverse orientation.

In some embodiments of the foregoing, the elongate shaft comprises at least a first and second elongate rib joined along the longitudinal axis, the first rib comprises has a pair of generally flat opposing side portions and an elongate edge portion, wherein the first set of detents comprises a plurality of flexible leaves extending from at least one of the first rib opposing side portions.

In some embodiments, the first set of detents comprises a plurality of symmetrically shaped, oppositely facing, flexible leaves extending from both of the first rib opposing side portions.

In some embodiments, the second rib comprises a pair of generally flat opposing side portions and an elongate edge portion; and wherein the first set of detents further comprises a plurality of flexible leaves from at least one of the second rib opposing side portions.

In some embodiments, the first set of detents comprises a plurality of symmetrically shaped, oppositely facing, flexible leaves extending from both of the second rib opposing side portions.

In some embodiments, the first and second elongate ribs are substantially parallel to one another.

In some embodiments, the opposing leaves on the first rib and the opposing leaves on the second rib are aligned with and symmetric to one another.

In some embodiments, all of the flexible leaves are of the same shape (e.g., a post, a flat "petal" or lobe, or the like).

Some embodiments of the foregoing further comprise a pair of elongate supporting ribs joined along the central axis (e.g., which supporting ribs divide supporting leaves on the first rib, from the supporting leaves on the second rib).

In some embodiments, each member of the first set of detents, and of the second set of detents when present, comprises in turn a detent subset (e.g., two, three, four, five, or six individual detents) extending laterally from the elongate shaft in the same plane (and are preferably uniformly shaped with one another and uniformly spaced from one another), so that the members of the subset exert dispersed, radially distributed, and/or substantially uniform pressure against the raised lip on the inside wall of the barrel, when the members of that detent subset encounter and pass the raised lip.

In some embodiments, each of the first and second sets of detents (e.g., the flexible leaf detents) are configured to provide an audible and/or tactile click to a user as forward motion of the plunger into the barrel causes each of the detents or detent subset to encounter and pas (e.g., flexes and releases) the raised lip.

In some embodiments, the first and second sets of detents both comprise flexible leaf detents, the syringe further comprising:

a third set of uniformly spaced, fixed raised detents formed on the elongate shaft and positioned to aid in arresting forward motion of the syringe plunger just after each member of the second set of detents elicits an audible and/or tactile "click" upon passage by the raised lip.

In some embodiments, the elongate shaft comprises or consists of an organic polymer (e.g., polypropylene).

In some embodiments, the hollow body comprises or consists of an organic polymer (e.g., polypropylene).

In some embodiments, the raised lip comprises an annular lip (e.g., a partial or complete ring-shaped lip, which may optionally have one or more openings, "notches" or "gates" formed therein).

In some embodiments, the raised lip is positioned adjacent the second opening (e.g., wherein the inside wall has a lower portion and an upper portion, and the raised lip is positioned in the upper portion, preferably proximate to or within 1 or 2 millimeters of the second open end).

In some preferred embodiments, the detents provide an audible sound or "click", a tactile sensation or "click", or both audible and tactile "clicks" to the user.

In some preferred embodiments, each member of the first set of detents is preferably symmetric with one another and configured to sequentially and releasably engage the lip when the plunger is depressed into the hollow body.

In some preferred embodiments, the syringe has a total injectable volume, with the first set of detents preferably configured to divide the total injectable volume into a plurality of separate, preferably uniform, injectable subvolumes.

In some embodiments, the syringe has a total injectable volume of from 1 or 2 milliliters to 5 or 10 milliliters, with the first set of detents (and when present the second set of detents) configured to divide the total injectable volume into at least 10 or 20 uniform injectable subvolumes, and up to 40 or 50 uniform injectable subvolumes; optionally but preferably wherein each of the uniform injectable subvolumes are not more than 1, 2, 5 or 10 percent different from one another.

A further aspect of the invention is a syringe as described herein, further comprising a sterile injectable pharmaceutical formulation (e.g. a formulation comprising botulinum toxin or lidocaine in a pharmaceutically acceptable aqueous carrier) contained therein.

A further aspect of the invention is a syringe as described herein, further comprising a rigid or flexible endoscope (e.g., a cystoscope) or guide cannula operatively coupled thereto.

A further aspect of the invention is, as a subcombination, the syringe plunger as described herein, free of and separate from, but preferably configured for insertion into, a syringe barrel as described herein.

Being more user friendly, easier to use and more accurate to work with, the present invention is described to replace all the common syringes. Furthermore, it is especially helpful in injection of botulinum toxin (e.g., into the bladder), anesthetics such as lidocaine and procaine/novocaine (e.g., into the gum), or other agents, whenever multiple subvolumes of solution from a single syringe should be injected into different spots in the body.

The present invention is explained in greater detail in the drawings herein and the specification set forth below.

DETAILED DESCRIPTION OF ILLUSTRATIVE EMBODIMENTS

The present invention is now described more fully hereinafter with reference to the accompanying drawings, in which embodiments of the invention are shown. This invention may, however, be embodied in many different forms and should not be construed as limited to the embodiments set forth herein. Instead, these embodiments are provided so that this disclosure will be efficiently convey non-limiting examples of the invention to those skilled in the art.

Like numbers refer to like elements throughout. In the figures, the thickness of certain lines, layers, components, elements or features may be exaggerated for clarity. Where used, broken lines illustrate optional features or operations unless specified otherwise.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof.

As used herein, the term "and/or" includes any and all possible combinations or one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with and/or contacting the other element or intervening elements can also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature can have portions that overlap or underlie the adjacent feature.

Spatially relative terms, such as "under," "below," "lower," "over," "upper" and the like, may be used herein for ease of description to describe an element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus the exemplary term "under" can encompass both an orientation of over and under. The device may otherwise be oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only, unless specifically indicated otherwise.

It will be understood that, although the terms first, second, etc., may be used herein to describe various elements, components, regions, layers and/or sections, these elements, components, regions, layers and/or sections should not be limited by these terms. Rather, these terms are only used to distinguish one element, component, region, layer and/or section, from another element, component, region, layer and/or section. Thus, a first element, component, region, layer or section discussed herein could be termed a second element, component, region, layer or section without departing from the teachings of the present invention. The sequence of operations (or steps) is not limited to the order presented in the claims or figures unless specifically indicated otherwise.

"Botulinum toxin" as used herein may be any suitable, pharmaceutically acceptable, and generally liquid injectible, formulation thereof, such as BOTOX® onabotulinumtoxin A from Allergan Inc.

FIGS. 1-3 show a first embodiment of the present invention. As illustrated, the device comprises a syringe plunger 10 received in a syringe body 11. The plunger has a seal engagement flange 12 on one end thereof, and an operator engagement flange 13 on the other end thereof. A seal or sliding seal member (not illustrated), generally formed of a flexible organic polymer material (e.g., rubber, thermoplastic elastomer (or "TPE"), etc.), is removably or permanently affixed to the seal engagement flange to force a liquid pharmaceutical formulation from the syringe body through the first (generally smaller) open end, or outlet port, 14, when the operator engagement flange is depressed.

The first open end or outlet port 14 may take any suitable form, such as a LEUER taper fitting, a LEUER-LOCK™ fitting, etc.

The syringe body may include laterally extending finger or gripping tabs 15, which are optionally but preferably positioned near the second (wider) open end (e.g., within 1 or 2 millimeters thereof).

The plunger itself comprises a plunger shaft 20, which is formed of one or more plunger ribs 21 (four ribs in the embodiment of FIGS. 1-3). A disc-shaped plunger retention detent 22 is formed in a manner extending laterally from the plunger ribs, and positioned near the seal engagement flange, to help prevent the plunger itself from being inadvertently fully withdrawn from the syringe body when the plunger is retracted (e.g., to draw a liquid pharmaceutical through the outlet port and into the syringe body for subsequent ejection therefrom).

As best shown in FIG. 3, the disc-shaped retention detent 22 is configured to abut against a raised lip 23 formed on the inside wall of the syringe body near the second opening. The raised lip may take any suitable form, including a continuous ring, a ring interrupted ring interrupted by notches or gates, etc., and may have any suitable profile (e.g., half-circle, triangular, rectangular, etc.). Likewise, the plunger retention detent may take any suitable shape, including interrupted or uninterrupted shapes, and have any suitable profile.

As shown in FIGS. 1-3, a first set of disc-shaped raised detents 30 is also provided on the plunger shaft, equally spaced along the length thereof, and configured to engage the raised lip. The detents are sufficiently large to cause perceptible, tactile, resistance to a human operator when the plunger is withdrawn from or depressed into the syringe body, but not so large as to prevent depression of the plunger into or withdrawal of the plunger from, the syringe body by the operator (optionally but preferably, with one-handed operation thereof). This first set of detents, while disc shaped like the plunger retention detent, may be shaped and/or sized differently therefrom, for example to provide lesser resistance to withdrawal than the plunger retention detent.

FIGS. 4-5 illustrate a second embodiment of the invention, similar to the embodiment of FIGS. 1-3, except that the set of detents are formed of discrete raised bumps 31 or segments on two of the four ribs, rather than as discs interconnecting the ribs. The raised detents on these two opposite ribs are aligned with one another so that they function together as a single set of detents, referred to as the first set of detents herein.

FIG. 6-7 illustrates a third embodiment of the invention, similar to the embodiment of FIGS. 4-5, except that the first set of detents are not substantially rigid and laterally projecting (as in FIGS. 1-5), but instead comprises a set of flexible fingers 32 extending laterally from two oppositely facing ones of the four plunger ribs.

FIGS. 8-9 illustrate a further embodiment of the invention having a first set of raised detents 33 formed on one rib thereof, and a second set of raised detents 36 formed on the opposite rib thereof. The first and second set of raised detents are equally spaced with, but slightly offset from, one another, to form a "trapping segment" 39 which retains the position of the syringe between each incremental injection segment.

Figure 1:
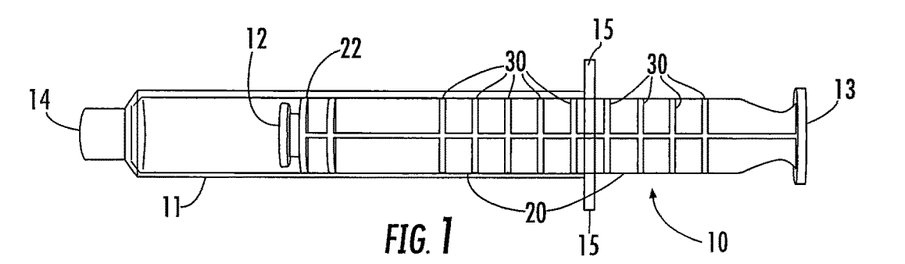
FIG. 1 is a side view of a first embodiment of the present invention.
Figure 2:
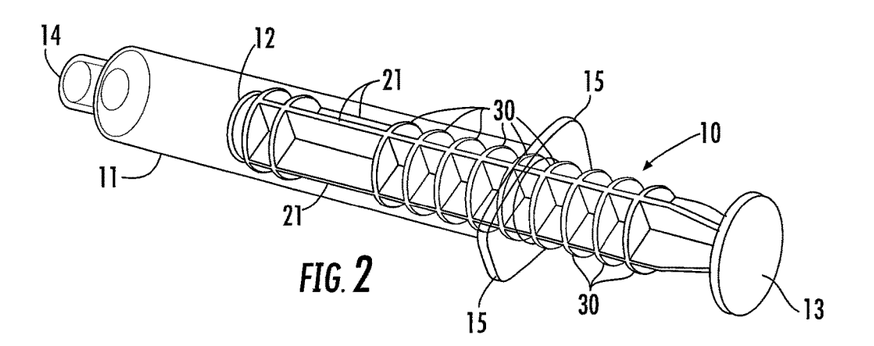
FIG. 2 is a perspective view of the embodiment of FIG. 1.
Figure 3:
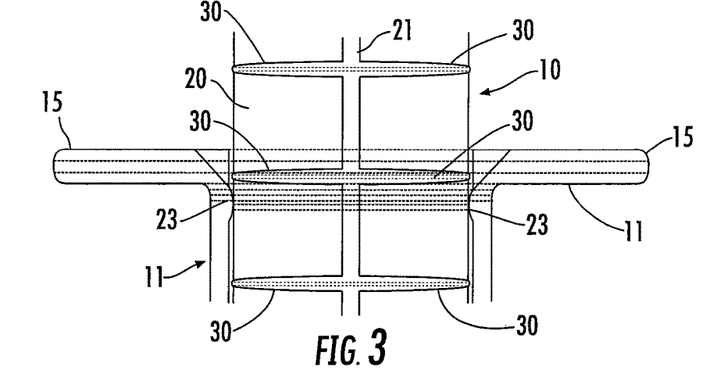
FIG. 3 is a side sectional view of the embodiment of FIG. 1.
Figure 4:
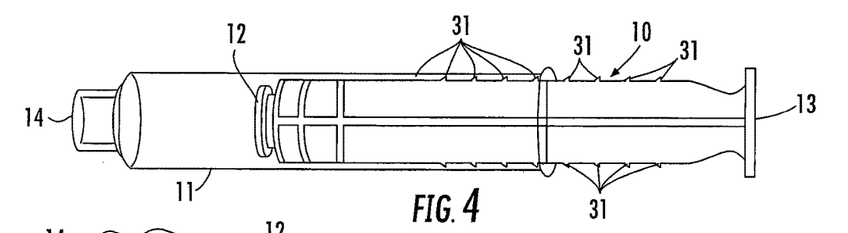
FIG. 4 is a side view of a second embodiment of the present invention.
Figure 5:
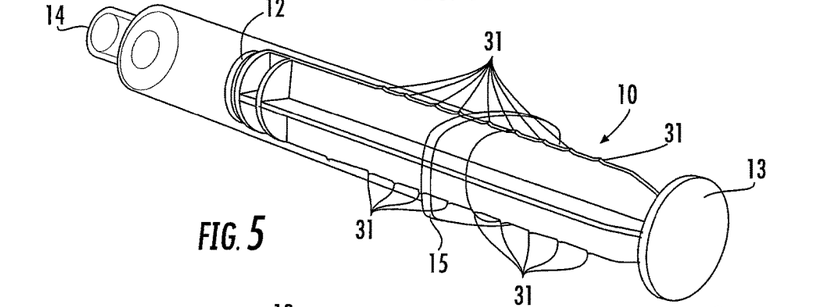
FIG. 5 is a perspective view of the embodiment of FIG. 4.
Figure 6:
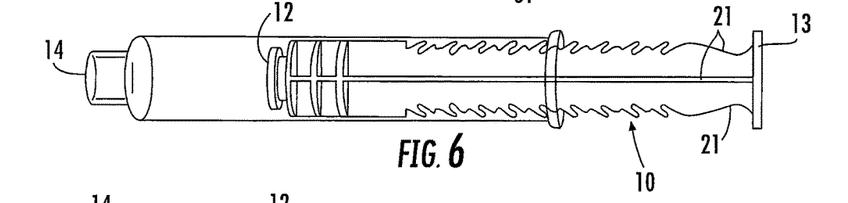
FIG. 6 is a side view of a third embodiment of the present invention.
Figure 7:
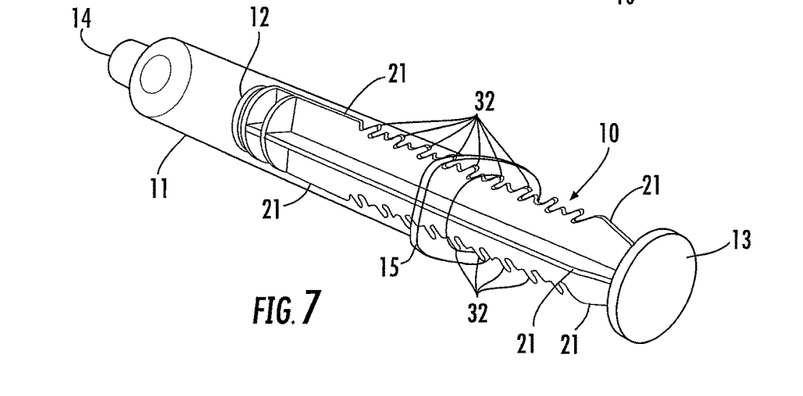
FIG. 7 is a perspective view of the embodiment of FIG. 4.
Figure 8:
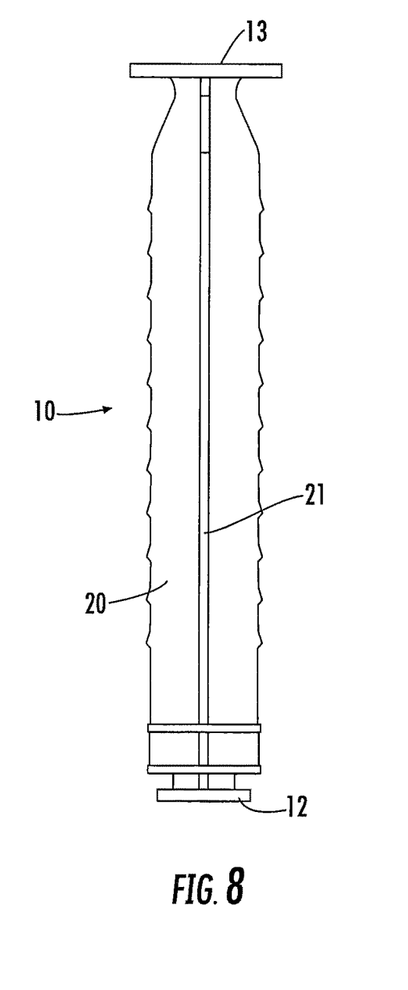
FIG. 8 is a side view of a plunger of a fourth embodiment of the present invention.
Figure 9:
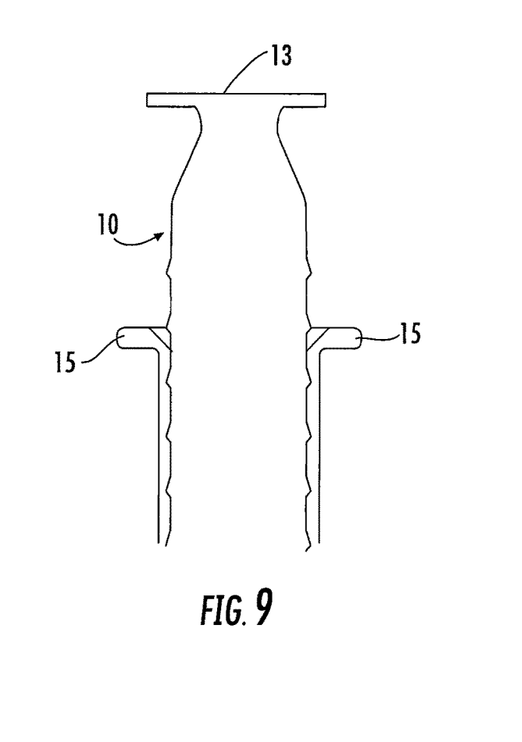
FIG. 9 is a side-sectional view of a plunger of FIG. 8 inserted in a syringe body.
Figure 10A:
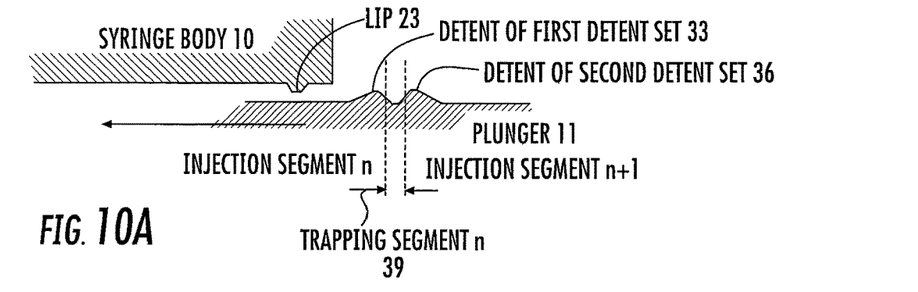
FIG. 10a is a side-sectional view of an embodiment of the present invention, showing the plunger sliding through an injection segment n.
Figure 10B:
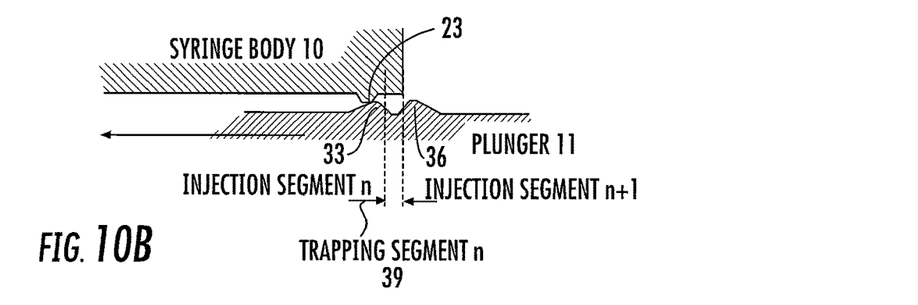
FIG. 10b is a side sectional view of the embodiment of FIG. 10a, showing the plunger transitioning from injection segment n into trapping segment n.
Figure 10C:
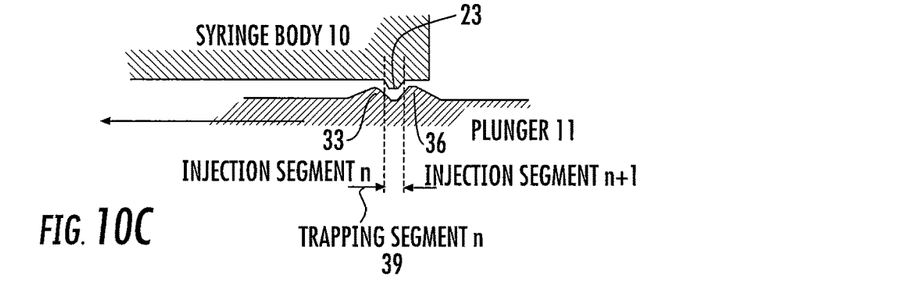
FIG. 10c is a side sectional view of the embodiment of FIG. 10a-10b, showing the plunger positioned in trapping segment n.
Figure 10D:
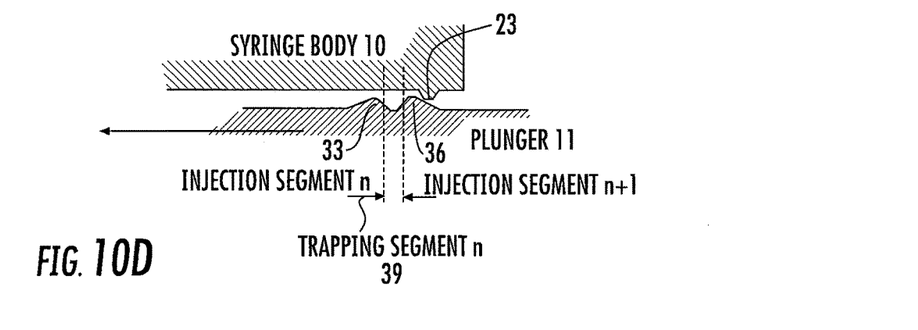
FIG. 10d is a side sectional view of the embodiment of FIG. 10a-10b, showing the plunger exited from trapping segment n and sliding through injection segment n+1.
Figure 11:
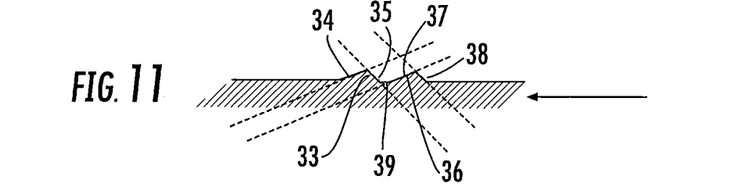
FIG. 11 is a side view of a further embodiment of the invention, illustrating cooperating pairs of detents formed from a first and second set of detents.
Figure 12:
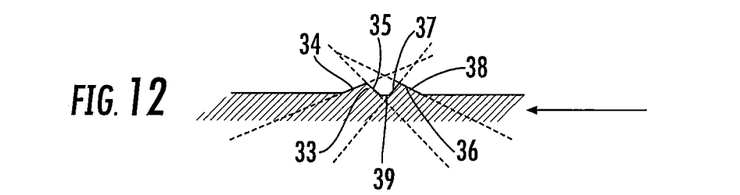
FIG. 12 is a side view of a further embodiment of the invention, illustrating cooperating pairs of detents formed from a first and second set of detents.
Figure 13:
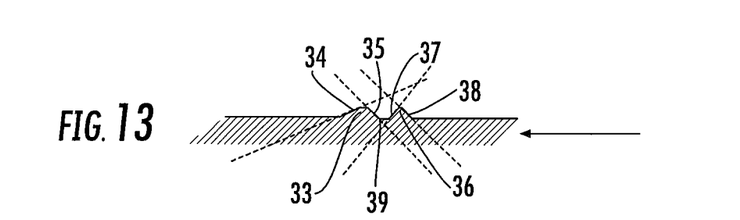
FIG. 13 is a side view of a further embodiment of the invention, illustrating cooperating pairs of detents formed from a first and second set of detents.
Figure 14:
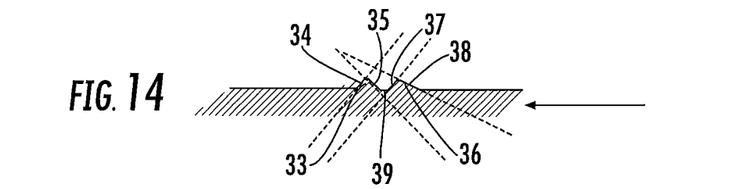
FIG. 14 is a side view of a further embodiment of the invention, illustrating cooperating pairs of detents formed from a first and second set of detents.
Figure 15:
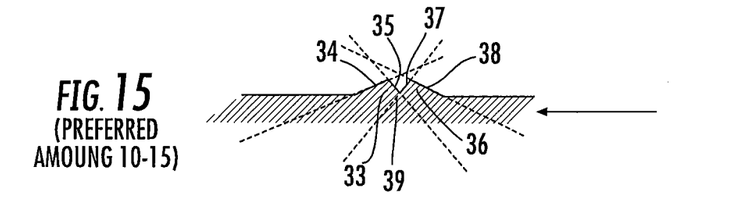
FIG. 15 is a side view of a further embodiment of the invention, illustrating cooperating pairs of detents formed from a first and second set of detents.

FIG. 10A-10B are detailed illustrations of an embodiment similar to that of FIGS. 8-9, except that the first and second set of detents 33, 36, are moved to the same rib, and a single member of each set is shown. The "trapping segment" 39 can be seen in between. As seen in FIG. 10A, the detents of the first set have a leading edge portion 34 and a trailing edge portion 35, with the slope of the trailing edge portion being greater (steeper) than the slope of the leading edge portion. The detents of the second set likewise have a leading edge portion 37 and a trailing edge portion 38, but in contrast the slope of the leading edge is greater (steeper) than the slope of the trailing edge. The purpose and result is that greater resistance is encountered by the operator when depressing the plunger and "leaving" a trapping segment (that is, beginning the next incremental injection) than encountered when entering the trapping segment (that is, ending each incremental injection), hence providing a tactile "click" that can be perceived by the operator. Numerous different configurations of slopes for leading edges and trailing edges can also be employed, as illustrated in FIGS. 11-15, and the sets of detents can be located on the same rib, on opposite ribs, or each set comprised of multiple cooperating members on multiple ribs, or even be formed of multiple disc-shape detents (for example, as illustrated with a single first set of detents in FIGS. 1-3).

Figure 16:
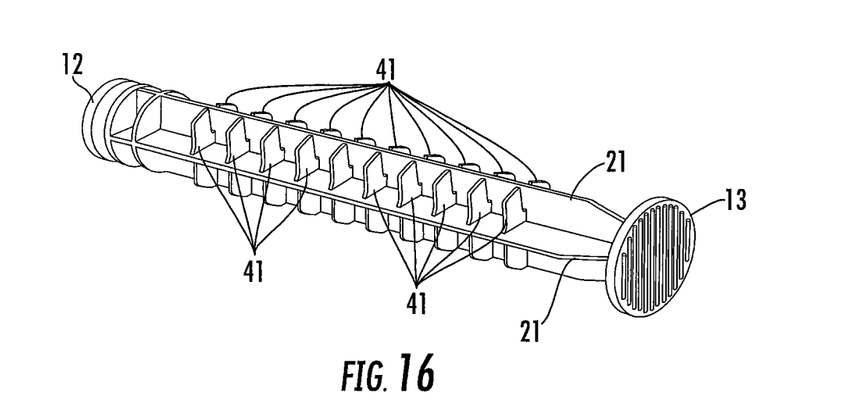
FIG. 16 is a perspective view of a further embodiment of the present invention.
Figure 17:
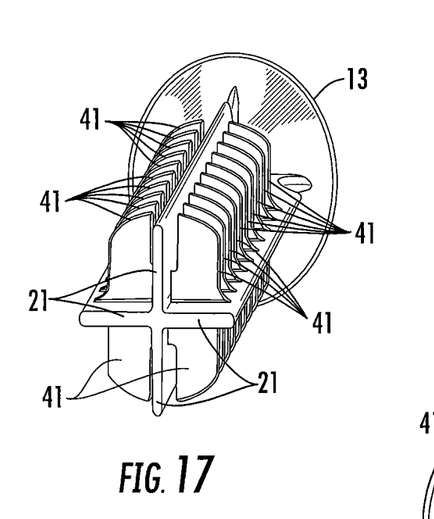
FIG. 17 is a further perspective view of the embodiment of FIG. 16, from an end orientation.
Figure 18:
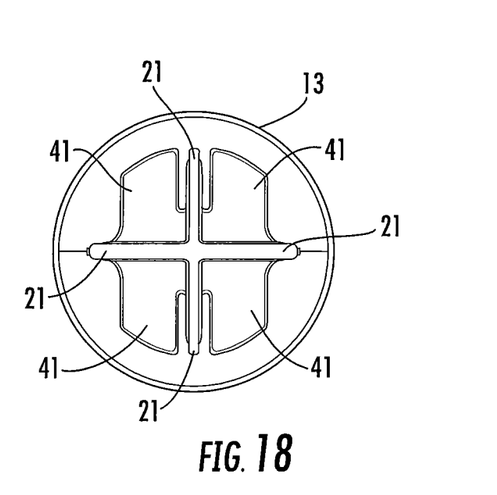
FIG. 18 is an end sectional view of the embodiment of FIGS. 16-17, showing the symmetric orientation of all four sets of flexible leaves.
Figure 19:
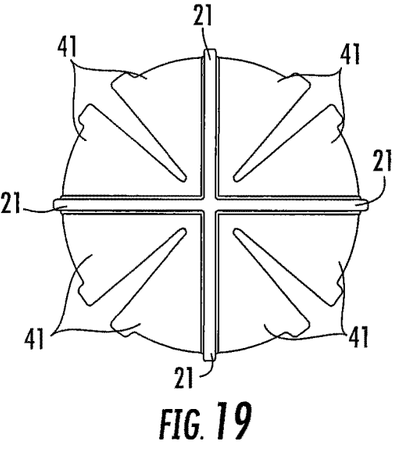
FIG. 19 is an end sectional view of an alternate embodiment of the invention.
Figure 20:
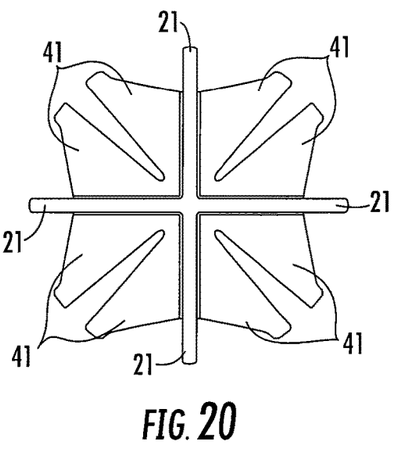
FIG. 20 is an end sectional view of an alternate embodiment of the invention.
Figure 21:
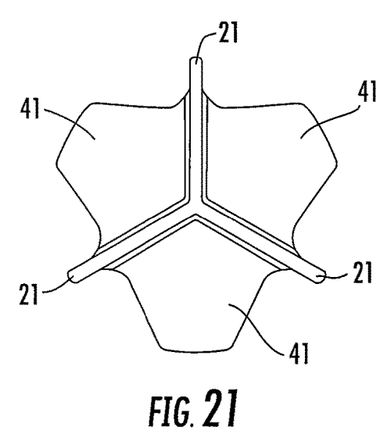
FIG. 21 is an end sectional view of an alternate embodiment of the invention.
Figure 22:
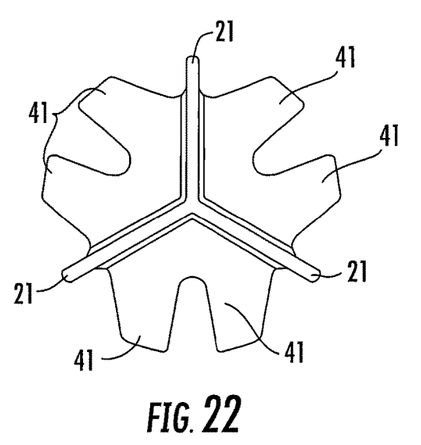
FIG. 22 is an end sectional view of an alternate embodiment of the invention.
Figure 23:
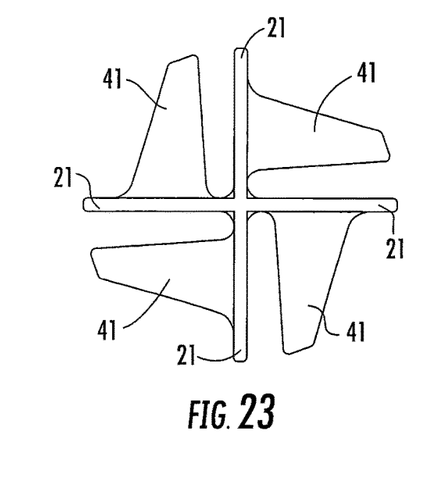
FIG. 23 is an end sectional view of an alternate embodiment of the invention.

FIGS. 16-18 illustrate an additional embodiment of the invention, including a first set of detents, where each detent is in the shape of a flexible leaf 41 extending from an elongate rib 21, which flexible leaf detents are flexed and released when they encounter the raised lip as the plunger is depressed into, or withdrawn from, the syringe body. Each leaf extends laterally from a side portion of one of the raised ribs (as more clearly seen in FIGS. 17-18). The flexible leaf detents (which may be in the shape of, petals, lobes, etc.), may take any suitable form, as shown by the non-limiting additional examples set forth in FIGS. 19-23. These leaves (or leaf subsets) optionally but preferably provide both an audible and tactile "click" to the user during operation of the syringe. Preferably the leaves are symmetrically shaped and symmetrically radially distributed around the plunger, to exert substantially uniform pressure on the lip 23, and syringe body, as they pass thereby. The edge portion of the leaf may be blunt, rounded, sharpened, etc., to tune the sound of the audible "click" created when each leaf (or leaf subset) is released by the lip 23.

Figure 24:
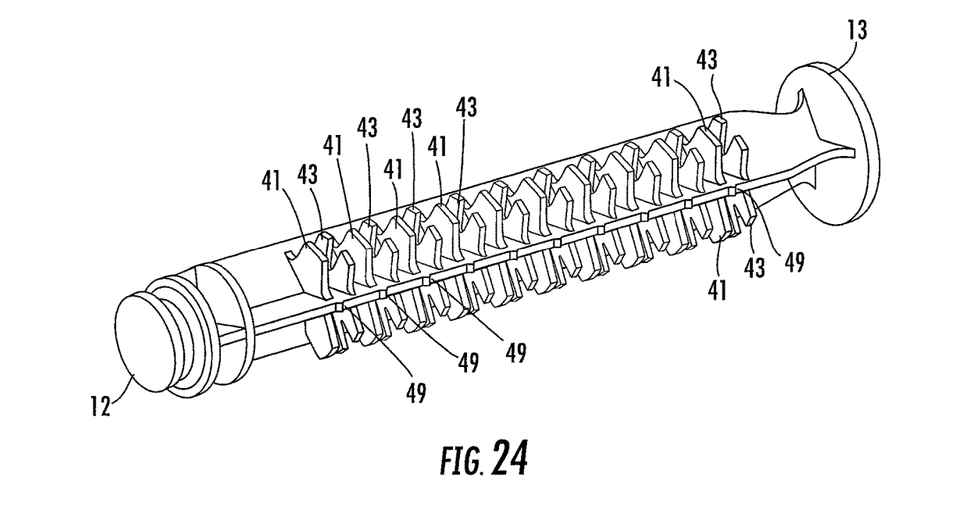
FIG. 24 is a perspective view of a further embodiment of the present invention, showing first and second sets of leaf detents configured to emit a "start" and "stop" click for each injection subvolume.
Figure 25:
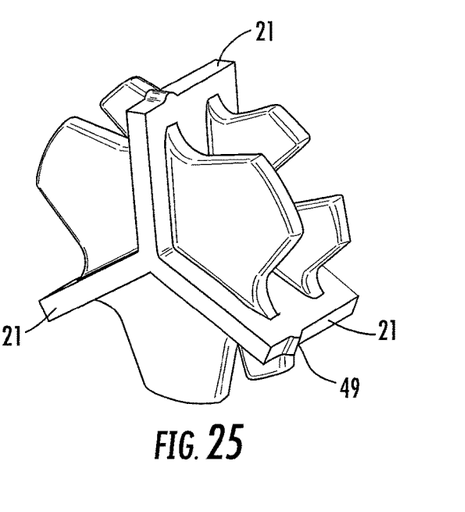
FIG. 25 is a detailed view of the embodiment of FIG. 24.

FIGS. 24-25 illustrate a still further embodiment of the invention employing a first set of flexible leaf detents 41 and a second set of flexible leaf detents 43, with a "trapping segment" (like that described in connection with FIGS. 8-15) formed therebetween. This embodiment preferably provides both an audible and tactile "click" to the user both upon ending one incremental injection, and upon beginning the next incremental injection. Different leaf configurations are used for the first and second set of detents to provide a different resistance, and/or provide a different feel or sound to the click. Note an optional third set of fixed detents 49 is also included, as best seen in FIG. 25, and as discussed further in connection with FIGS. 26-27 below.

Figure 26:
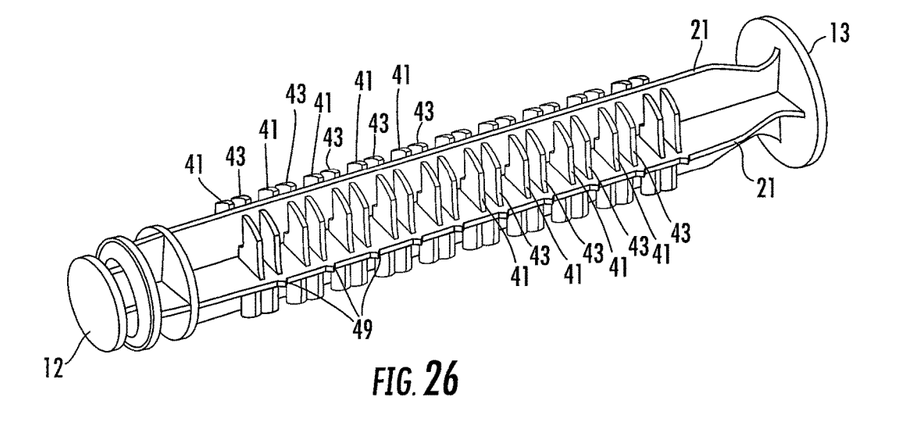
FIG. 26 is a perspective view of a still further embodiment of the present invention, showing first and second sets of leaf detents configured to emit a "start" and "stop" click for each injection subvolume, and a third set of detents configured to aid in stopping or arresting forward travel of the plunger into the barrel at the conclusion of injection of each incremental subvolume.
Figure 27:
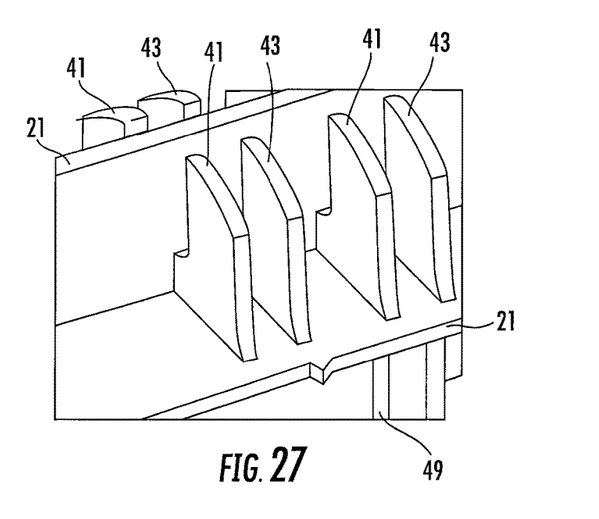
FIG. 27 is a detailed view of the embodiment of FIG. 26.

FIGS. 26-27 illustrate a still further embodiment, similar to that of FIGS. 24-25, except that the leaves of both the first and second set of flexible detents 41, 43 are similarly configured, and a third set of fixed detents 49 are also provided, aligned with the detents of the second set. This third set provides a greater resistance to overcome to leave a trapping segment and begin a next incremental injection, than required to enter the trapping segment upon entering the trapping segment. However, a tactile and/or audible click is provided both upon entering and exiting each trapping segment.

In all of the foregoing, the plunger or elongate shaft may comprise or consist of an organic polymer (e.g., polypropylene). Likewise, the hollow body may comprise or consist of an organic polymer (e.g., polypropylene). The seal (not shown) may also be formed of an organic polymer, but generally a different material, that is elastic, such as natural or synthetic rubber or a thermoplastic elastomer (TPE).

In all of the foregoing, the syringe may having a total injectable volume of from 1 or 2 milliliters to 5, 10 or 30 milliliters, or more, with the first set of detents (and when present said second set of detents) configured to divide said total injectable volume into at least 5, 10 or 20 uniform injectable subvolumes, and up to 40 or 50 uniform injectable subvolumes. Optionally but preferably, each of injectable subvolumes are not more than 1, 2, 5 or 10 percent different from one another.

Any of the foregoing syringes may be loaded with any suitable pharmaceutical formulation, such as a sterile injectable pharmaceutical formulation (e.g. a formulation comprising botulinum toxin or lidocaine in a pharmaceutically acceptable aqueous carrier) contained therein. In some embodiments, an injection needle (optionally with a removable or retractable cover to help minimize inadvertent "needle sticks") may be fixed to or operatively associated with the outlet opening. Depending on the intended use, a rigid or flexible endoscope (e.g., a cystoscope) or guide cannula may be operatively coupled to the syringe outlet opening.

While the invention has been described above substantially as a combination of a syringe plunger with a syringe barrel and seal, it will be appreciated that the syringe plunger may be provided as a subcombination part alone, useful for subsequent assembly into a complete syringe as described herein.

The foregoing is illustrative of the present invention, and is not to be construed as limiting thereof. The invention is defined by the following claims, with equivalents of the claims to be included therein.

That which is claimed is:

1. A syringe, comprising:
  (a) an elongate hollow body having a first open end, an inside wall, a second open end, and a continuous annular raised lip on said inside wall;
  (b) a syringe plunger positioned in said elongate hollow body through said second open end, said syringe plunger comprising:
    (i) an elongate shaft having a longitudinal axis, an upper end portion and a lower end portion;
    (ii) a seal connected to said lower end portion;
    (iii) a flange connected to said upper end portion;
    (iv) a plurality of elongate ribs joined along said longitudinal axis, each rib comprising opposing side portions and an elongate edge portion; and
    (v) a first set of detent subsets formed on said elongate shaft aligned with said longitudinal axis;
  with each detent subset configured to sequentially and releasably engage said raised lip when said syringe plunger is moved within said elongate hollow body;
  said syringe having a total volume, with said first set of detent subsets configured to divide said total volume into a plurality of separate subvolumes;

wherein each detent subset comprises at least one flexible leaf extending from at least one opposing side portion, said flexible leaf having a perimeter comprising:
a coupling portion coupled to at least one of said opposing side portions;
a detent portion configured to engage said raised lip; and
an edge portion disposed between said coupling portion and said detent portion and disposed inward toward the longitudinal axis with respect to the detent portion so as to prevent engagement of said edge portion with said raised lip.

2. The syringe of claim 1, wherein said elongate shaft comprises at least three elongate ribs joined along said longitudinal axis.

3. The syringe of claim 1, wherein each detent subset comprises at least two flexible leaves extending from at least two opposing side portions.

4. The syringe of claim 1, wherein said first set of detent subsets is formed on only one of said elongate ribs.

5. The syringe of claim 1, further comprising a second set of detent subsets formed on said elongate shaft in a linear and uniformly spaced pattern thereon aligned with said longitudinal axis,
with said second set of detent subsets positioned in offset alignment with said first set of detent subsets, wherein the first and second sets of detent subsets together are configured to define on said elongate shaft: (i) a plurality of uniformly sized, injection segments, and (ii) a plurality of uniformly sized trapping segments in a sequential alternating arrangement with said injection segments.

6. The syringe of claim 5, wherein:
said elongate shaft comprises at least three elongate ribs joined along said longitudinal axis; and
said flexible leaves of said first and second sets of detent subsets extend from the same opposing side portions.

7. The syringe of claim 5, wherein said first set of detents and said second set of detents are substantially symmetric with one another in reverse orientation.

8. The syringe of claim 1, wherein said first set of detent subsets comprises a plurality of symmetrically shaped, oppositely facing, flexible leaves extending from said opposing side portions of a first elongate rib of said plurality of elongate ribs.

9. The syringe of claim 1, wherein said first set of detent subsets comprises at least one flexible leaf extending from at least one of said opposing side portions of at least two of said plurality of elongate ribs.

10. The syringe of claim 8, wherein said first set of detent subsets comprises a plurality of symmetrically shaped, oppositely facing, flexible leaves extending from opposing side portions of a second elongate rib of said plurality of elongate ribs.

11. The syringe of claim 10, wherein said first and second elongate ribs are substantially parallel to one another.

12. The syringe of claim 11, wherein said opposing side portions on said first elongate rib and said opposing side portions on said second elongate rib are aligned with and symmetric to one another.

13. The syringe of claim 3, wherein all of said flexible leaves are of the same shape.

14. The syringe of claim 1, wherein each subset of said first set of detent subsets comprises a plurality of flexible leaves extending laterally from said elongate shaft in the same plane, so that the flexible leaves of said detent subset exert dispersed, radially distributed, and/or substantially uniform pressure against said raised lip on said inside wall of said elongate hollow body, when the flexible leaves of said detent subset encounter and pass said raised lip.

15. The syringe of claim 1, wherein each of said at least one flexible leaf of said first set of detent subsets is configured to provide an audible and/or tactile click to a user as forward motion of said syringe plunger into said elongate hollow body causes said each of said at least one flexible leaf of said first set of detent subsets to encounter and pass said raised lip.

16. The syringe of claim 5, further comprising:
a third set of uniformly spaced, fixed raised detents formed on said elongate shaft and positioned to aid in arresting forward motion of said syringe plunger just after each member of said second set of detent subsets elicits an audible and/or tactile "click" upon passage by said raised lip.

17. The syringe of claim 1, wherein said elongate shaft comprises an organic polymer.

18. The syringe of claim 1, wherein said hollow elongate body comprises an organic polymer.

19. The syringe of claim 1, wherein said raised lip is positioned adjacent said second open end.

20. The syringe of claim 1, said syringe having a total injectable volume of from 1 milliliter to 10 milliliters, with said first set of detent subsets configured to divide said total injectable volume into at least 10 uniform injectable subvolumes, and up to 50 uniform injectable subvolumes.

21. The syringe of claim 1, further comprising a sterile injectable pharmaceutical formulation contained therein.

22. A syringe plunger comprising:
(i) an elongate shaft having a longitudinal axis, an upper end portion and a lower end portion;
(ii) a seal connected to said lower end portion;
(iii) a flange connected to said upper end portion;
(iv) a plurality of elongate ribs joined along said longitudinal axis, each rib comprising opposing side portions and an elongate edge portion; and
(v) a first set of detent subsets formed on said elongate shaft aligned with said longitudinal axis;
with each detent subset configured to sequentially and releasably engage a continuous annular raised lip on an inside wall of a corresponding syringe hollow body when said syringe plunger is moved within the corresponding syringe hollow body;
wherein each detent subset comprises at least one flexible leaf extending from at least one opposing side portion, said flexible leaf having a perimeter comprising:
a coupling portion coupled to at least one of said opposing side portions;
a detent portion configured to engage said raised lip; and
an edge portion disposed between said coupling portion and said detent portion and disposed inward toward the longitudinal axis with respect to the detent portion so as to prevent engagement of said edge portion with said raised lip.

23. The syringe plunger of claim 22, wherein each flexible leaf of the first set of detent subsets is configured to sequentially and releasably engage said raised lip when said syringe plunger is displaced for every unit of medication aspirated and/or dispensed.

24. The syringe of claim 1, wherein each flexible leaf of the first set of detent subsets is configured to sequentially and releasably engage the raised lip when the syringe plunger is withdrawn from the elongate hollow body.

25. The syringe of claim 1, wherein the detent subsets of the first set of detent subsets are uniformly spaced.

* * * * *

UNITED STATES PATENT AND TRADEMARK OFFICE
CERTIFICATE OF CORRECTION

PATENT NO.        : 10,398,847 B2
APPLICATION NO.   : 14/966326
DATED             : September 3, 2019
INVENTOR(S)       : Mizrazadeh et al.

Page 1 of 1

It is certified that error appears in the above-identified patent and that said Letters Patent is hereby corrected as shown below:

On the Title Page

Item (73), "Wake Forrest University Health Sciences" should read, "Wake Forest University Health Sciences"

Signed and Sealed this
Seventh Day of April, 2020

Andrei Iancu
*Director of the United States Patent and Trademark Office*